US00PP14682P39

(12) United States Plant Patent
Fear

(10) Patent No.: US PP14,682 P3
(45) Date of Patent: Apr. 6, 2004

(54) BLACKBERRY PLANT NAMED 'DRISCOLL SONOMA'

(50) Latin Name: *Rubus L. subgenus Rubus*
Varietal Denomination: Driscoll Sonoma

(75) Inventor: Carlos D. Fear, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/772,330

(22) Filed: Jan. 29, 2001

(65) Prior Publication Data

US 2003/0172422 P1 Sep. 11, 2003

(51) Int. Cl.[7] ..... A01H 5/00

(52) U.S. Cl. ..... Plt./203

(58) Field of Search ..... Plt./203

*Primary Examiner*—Bruce R. Campell
*Assistant Examiner*—June Hwu
(74) *Attorney, Agent, or Firm*—Pennie & Edmonds LLP

(57) ABSTRACT

The present invention relates to a new and distinct cultivar of blackberry plant named 'Driscoll Sonoma'. The new cultivar is distinguished from other blackberry cultivars by its fruit of excellent fruit flavor and shipping quality. 'Driscoll Sonoma' is a thornless mid-late season cultivar. The new cultivar is distinguished from its seed parent by its larger fruit and greater plant vigor. The new cultivar is distinguished from its pollen parent by its larger, better flavored fruit.

2 Drawing Sheets

Latin name of the genus and species of the plant claimed: The variety is botanically identified as *Rubus L. subgenus Rubus.*

BACKGROUND OF THE INVENTION

This invention relates to a new cultivar of blackberry called 'Driscoll Sonoma'. The new cultivar was developed from hybridization of the patented female cultivar 'Navaho', U.S. Plant Pat. No. 6,679, with the unpatented male cultivar 'Hull Thornless'. The parents were crossed in Spring 1991 whereafter fruit and seed were collected to produce seedlings for field planting in Watsonville, Calif. in 1991. The new cultivar was selected in July 1993 for its good flavor, thornless canes, season of production and firm, attractive fruit. The cultivar has been asexually propagated, and reproduced true to type plants by in vitro shoot tip culture. The cultivar has been asexually propagated and reproduced true-to-type plants by in vitro shoot tip culture.

SUMMARY OF THE INVENTION

The present invention provides a new and distinct blackberry cultivar named 'Driscoll Sonoma'. The variety is botanically identified as *Rubus L. subgenus Rubus*. The new cultivar produces a floricane crop which begins in early July and continues until mid-September. The new blackberry variety is distinguished from other varieties by a number of characteristics as set forth in Table 1. In particular, the new cultivar is distinguished by its thornless canes with fruit of excellent flavor and firmness which ripens at a time of the year when few other similar cultivars exist.

COMPARISON TO SIMILAR VARIETIES

The varieties that we believe to be similar to 'Driscoll Sonoma' from those known to us are the male parent 'Hull Thornless' and 'Chester', both unpatented cultivars. 'Driscoll Sonoma' is particularly different from these cultivars by having slightly larger, more uniform shaped fruit, by ripening earlier, and having a less acidic flavor. Further detailed comparison to 'Chester' is presented in Table 1.

BRIEF DESCRIPTION OF THE DRAWINGS

The accompanying photographs show typical specimens of the fruit, leaves and shoot of the new cultivar, in color as nearly true as reasonably possible in color illustrations of this type.

DESCRIPTION OF THE NEW VARIETY

Figure 1:
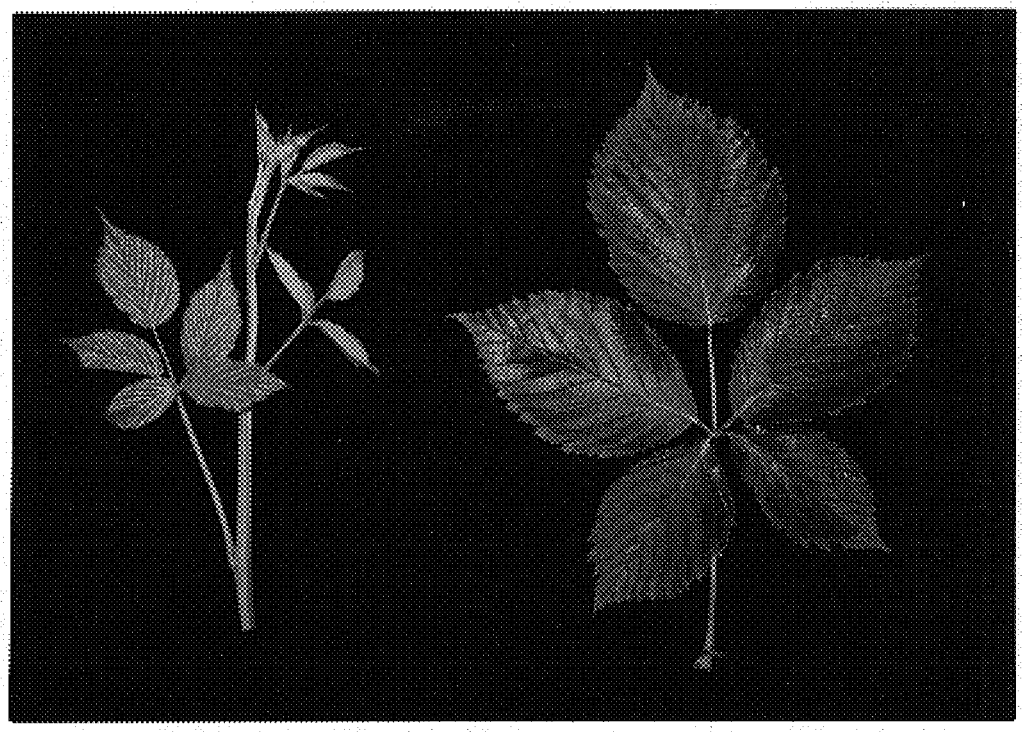
FIG. 1 is a photograph showing a primocane shoot and mature leaf of 'Driscoll Sonoma'.
Figure 2:
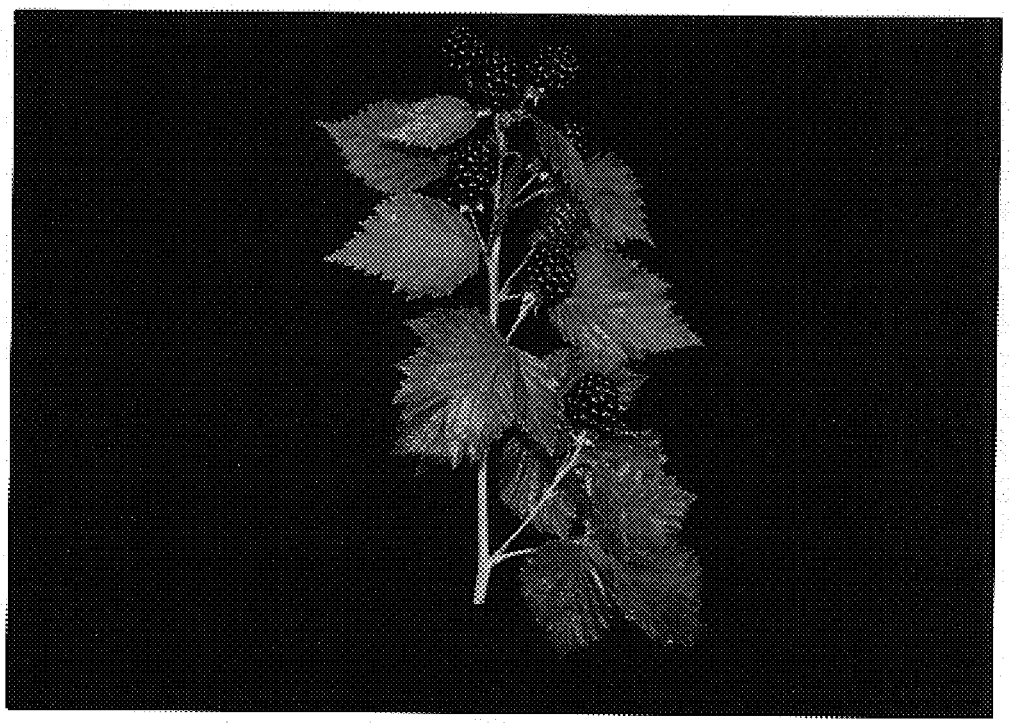
FIG. 2 is a photograph of a 'Driscoll Sonoma' fruiting lateral with fruit in various stages of development.

The following detailed description of the new blackberry cultivar, 'Driscoll Sonoma', is based upon recorded observations of plants and fruit grown between 1996 and 2000 in Watsonville, Calif., and is believed to apply to plants of the 'Driscoll Sonoma' cultivar grown in similar conditions of soil and climate elsewhere. The description is based on recorded observations of 2–5 year old plants. Plants were grown in soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

CHARACTERISTICS OF THE NEW VARIETY

'Driscoll Sonoma' can be characterized by numerous characteristics. The average priomcane length is 213 cm. The primocane color is N186C (in R.H.S. Colour Chart) on the exposed side and 144A (in R.H.S. Colour Chart) on the shaded side. The floricance color is 146C (in R.H.S. Colour Chart) on both the exposed and shaded sides. The relief between the veins of the leaf of 'Driscoll Sonoma' is weak, meaning there are very minor undulations between the veins and the leaves are nearly flat. The leaf surface has a few small soft hairs on the upper and lower surfaces. The petiole color is N186C (in R.H.S. Colour Chart). The stipule length averages 13 mm, width 1.2 mm, and color 144A (in R.H.S. Colour Chart). Bud burst in Watsonville, Calif. is late relative to most cultivars. Usually bud burst occurs from mid March to early April. Flowering lasts for 3–5 weeks and usually begins in late April to early May. The petals of 'Driscoll Sonoma' are five per flower, ovate in shape, and N155B in color (in R.H.S. Colour Chart). The average length of the pedicel is short, 25 mm. The sepals of 'Driscoll Sonoma' are five per flower, and 138B in color (in R.H.S. Colour Chart). The seeds weigh about 3.4 mg and are approximately 3.2 mm long and about 1.9 mm wide. 'Driscoll Sonoma' is most suitable for market use as a highly flavored fresh market cultivar. 'Driscoll Sonoma' has been successfully shipped for long distance under refrigerated storage and has remained in good condition for up to about 10 days when kept under cold storage conditions.

Table 1 provides information on the plant and fruit characteristics of the new blackberry cultivar, 'Driscoll Sonoma', compared with characteristics of the unpatented blackberry cultivars, 'Olallie' and 'Chester'. Both 'Olallie' and 'Chester' are currently important cultivars for fresh market shipping, and thus are comparable to the proposed use of the new invention, 'Driscoll Sonoma'. Observations of 'Driscoll Sonoma' and 'Chester' were taken in side-by-side comparison in 1999 and 2000. The yield of 'Driscoll Sonoma' is medium, meaning an average yield of about 14,000 pounds per acre in comparison to Olallie which averages around 21,000 pounds per acre.

The new blackberry cultivar is particularly characterized and distinguished from other cultivars by its fruit with excellent flavor and shipping quality. The fruit of 'Driscoll Sonoma' is very attractive with a solid black color that rarely shows post harvest drupelet color reversion.

The canes of 'Driscoll Sonoma' are thornless and of low to moderate vigor until well established. Yield of the new cultivar is moderate in comparison with other varieties.

Driscoll Sonoma is distinguished from its pollen parent, 'Hull Thornless', by being earlier, less vigorous, and having larger less acidic fruit. Driscoll Sonoma is distinguished from its seed parent, 'Navaho', by having greater vigor and larger fruit.

TABLE 1

PLANT CHARACTERISTICS OF 'DRISCOLL SONOMA'

| | *Driscoll* Sonoma | Olallie | Chester |
|---|---|---|---|
| GENERAL | | | |
| Vigor | Low-moderate | Moderate-high | high |
| Growth habit | semi-upright | trailing | semi-upright |
| Productivity | medium | high | high |
| Self fruitfulness | yes | yes | yes |
| Number of young shoots | medium | medium | medium |

TABLE 1-continued

PLANT CHARACTERISTICS OF 'DRISCOLL SONOMA'

| | *Driscoll* Sonoma | Olallie | Chester |
|---|---|---|---|
| CANES | | | |
| Primocanes | | | |
| Anthocyanin coloration | absent | present | present |
| Spines | absent | present | absent |
| color | — | purple | — |
| attitude of tip | — | horizontal | — |
| texture | — | heavy | — |
| presence and distribution on petioles | absent | present; irregularly distributed | absent |
| density in central third of shoot | — | medium | — |
| Internodal distance (cm) - central third of mature cane | 3 | 2.6 | 3.1 |
| Glaucosity on full grown shoot | weak | weak | weak |
| Strength of full grown shoot | strong | medium | strong |
| Cane cross section | angular | rounded to angular | angular to grooved |
| LEAVES | | | |
| Relief between veins | medium | medium | medium |
| Number of leaflets | usually 5 | usually 3 | usually 5 |
| Leaf color | medium | medium | light |
| upper side | 139A, 147A | 137A, 137B | 147A |
| underside | 147B | 147B | 146A |
| Glossiness of upper surface | medium | medium | dull |
| Leaf cross section | concave | concave-flat | concave |
| Terminal leaflet | | | |
| length (cm) | 10.8 | 8.9 | 11.1 |
| width (cm) | 8.5 | 7.6 | 9 |
| shape | cordate | cordate | cordate |
| tip | acuminate | acuminate | acuminate |
| base | rounded | cordate | cordate |
| margin | double serrate | double serrate | double serrate |
| Lateral leaflet | | | |
| overlap of lateral leaflets | overlapping | overlapping | overlapping |
| length (cm) | 10.3 | 8.7 | 10.2 |
| width (cm) | 7.1 | 6.1 | 7.1 |
| shape | ovate | ovate | ovate |
| tip | acuminate | acuminate | acute |
| base | rounded to acute | acute | acute |
| margin | double serrate | double serrate | serrate |
| Petiole | | | |
| mean length (cm) | 9.4 | 5.3 | 7.9 |
| range | 7.3–11.1 | 3.6–8.7 | 3.9–10.2 |
| pigmentation of upper surface | reddish | green-slightly pink | purple |
| pigmentation of underside | green | green-slightly pink | green-pinkish |
| Length of stalklet | short | very short | medium |
| Rachis length (cm) between terminal and adjacent lateral leaflets) | 3.8 | 2.8 | 3.1 |
| Stipule orientation | erect | variable; clasping to erect | erect |
| FLOWERS | | | |
| Time of bud burst | late | early | late |
| Time of beginning | late | early | late |

TABLE 1-continued

PLANT CHARACTERISTICS OF 'DRISCOLL SONOMA'

| | *Driscoll* Sonoma | Olallie | Chester |
|---|---|---|---|
| of flowering | | | |
| Flower size | medium-large | small to medium | small to medium |
| Petal size | | | |
| length (mm) | 19.6 | 16.5 | 18.3 |
| width (mm) | 14 | 11.7 | 10.9 |
| Anthocyanin color of pedicel | absent | absent | present |
| Intensity of pedicel coloration | — | — | weak |
| Length of pedicel | short | long | short |
| Flower number (third node from tip of lateral) | 1.25 | 3.6 | 2 |
| FRUIT | | | |
| Harvest season | mid-late | early | mid-late |
| Dimensions | | | |
| weight (g/fruit) | 3.6 | 5.2 | 3.2 |
| size | medium-small | medium | small |
| length (cm) | 2.4 | 3.3 | 1.9 |
| width (cm) | 2.1 | 1.4 | 1.9 |
| Fruiting lateral length (in mid cane) | medium-long | medium | medium-long |
| mean number of fruit per lateral | 11.6 | 6.2 | 22.8 |
| range | 8–16 | 3–9 | 17–40 |
| Shape | ovate to elliptic longer than broad | narrow ovate much longer than broad | round to ovate as long as broad |
| Color | black | purple-black to black | black |

TABLE 1-continued

PLANT CHARACTERISTICS OF 'DRISCOLL SONOMA'

| | *Driscoll* Sonoma | Olallie | Chester |
|---|---|---|---|
| immature | 183A | 178A–183B | 184A |
| maturing | 187A | 187A | 200A–202A |
| mature | 202A | 200A | 202A |
| Firmness | medium | medium | firm |
| Glossiness | medium | medium-strong | medium |
| Soluble solids | 12 | 9.7 | 9.9 |
| Titratable acidity (% as citric acid) (ml of added 0.1 N NaOH to pH 8.1) | 9 | 13.3 | 9.9 |
| Number of drupelets per fruit | 60 | 86 | 40 |

NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of Driscoll Sonoma, Chester, and Olallie yielded DNA fragment patterns that uniquely distinguish each of these genetically distinct genotypes.

We claim:

1. A new and distinctive cultivar of blackberry plant, substantially as shown and described.

* * * * *